United States Patent [19]

Coon

[11] 3,978,046
[45] Aug. 31, 1976

[54] PREPARATION OF OCTAHYDRO-1,3,5,7-TETRAALKANOYL-1,3,5,7-TETRAZOCINES

[75] Inventor: Clifford L. Coon, Fremont, Calif.

[73] Assignee: The United States of America as represented by the Secretary of the Army, Washington, D.C.

[22] Filed: Feb. 4, 1975

[21] Appl. No.: 546,859

[52] U.S. Cl. .................. 260/239 BC; 260/239 HM
[51] Int. Cl.² ...................................... C07D 257/02
[58] Field of Search ............... 260/239 BC, 239 HM

[56] References Cited
UNITED STATES PATENTS 3,178,430  4/1965  Thatcher ..................... 260/239 HM

OTHER PUBLICATIONS

Emmons et al., J.A.C.S., vol. 74, pp. 5524 and 5525, (1952).

*Primary Examiner*—Nicholas S. Rizzo
*Assistant Examiner*—D. B. Springer
*Attorney, Agent, or Firm*—Nathan Edelberg; A. Victor Erkkila

[57] ABSTRACT

Octahydro-1,3,5,7-tetraalkanoyl-1,3,5,7-tetrazocines are produced by acting a methylene-bis-alkanecarboxamide with formaldehyde. The reaction carried out by heating the reactants in the presence of an acidic catalyst an inert organic liquid under substantially anhydrous conditions.

5 Claims, No Drawings

PREPARATION OF OCTAHYDRO-1,3,5,7-TETRAALKANOYL-1,3,5,7-TETRAZOCINES

BACKGROUND OF THE INVENTION

HMX (octahydro-1,3,5,7-tetranitro-1,3,5,7-tetrazocine) is the most powerful non-nuclear military explosive in military use at present. It is conventionally manufactured by nitrolysis of hexamethylenetetramine by a modification of the Bachmann process for RDX (hexahydro-1,3,5-trinitro-s-triazine). HMX can also be produced by nitrolysis of TAT (octahydro-1,3,5,7-tetracetyl-1,3,5,7-tetrazocine), which is currently prepared by acetolysis of hexamethylenetetramine. However, in addition to TAT, that process also produces the undesirable six-membered ring analogue, TRAT (hexahydro-1,3,5-triacetyl-s-triazine).

SUMMARY AND DETAILED DESCRIPTION OF THE INVENTION

In accordance with this invention there is provided a novel process for producing TAT and its homologues, which comprises reacting a methylene-bis-alkanecarboxamide with formaldehyde. The reaction can be carried out in the presence of an acid catalyst and an inert organic liquid under substantially anhydrous conditions. The reaction is represented as follows:

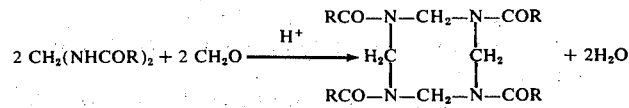

wherein R is an alkyl radical of 1 to 20 carbon atoms.

This reaction is unique in that it represents the first instance of the formation of an unbridged tetraazacyclooctane compound directly from noncyclic intermediates.

The process of the present invention can be effected by heating a mixture of the methylene-bis-alkanecarboxamide of the foregoing general formula, formaldehyde, an acid catalyst and an inert organic liquid under substantially anhydrous conditions to reaction temperatures, e.g., from 75° to 135°C. The substantially anhydrous conditions can be achieved by distilling the reaction water, as it is formed, from the reaction mixture, e.g., as an azeotropic mixture with the inert organic liquid employed.

Theoretically, the reaction of the present invention proceeds by condensation of 2 mols of the methylene-bis-alkanecarboxamide with 2 mols of formaldehyde such as to preclude the formation of the six-membered ring compound and yield only the desired HMX precursor, viz.

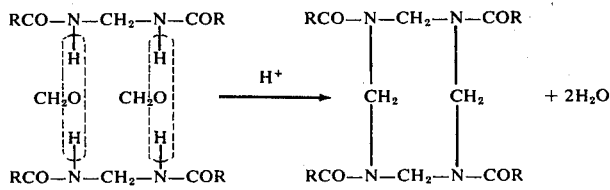

wherein R has the aforementioned definition. However, besides this desired reaction, other reactions take place to varying degrees, depending on the reaction conditions, which reduce the yield of the desired tetrazocine compound.

Examples of methylene-bis-alkanecarboxamides of the foregoing general formula, which can be reacted with formaldehyde to produce the corresponding octahyro-1,3,5,7-tetraalkanoyl-1,3,5,7-tetrazocine compounds according to the present invention, are methylene-bis-acetamide, methylene-bis-propionamide, methylene-bis-capramide, methylene-bis-lauramide and methylene-bis-stearamide.

Equimolecular proportions of formaldehyde and methylene-bis-alkanecarboxamide can be effectively employed in carrying out the process of the present invention, although the proportions of these reactants can be varied considerably. An excess of formaldehyde is advantageously utilized to offset loss of formaldehyde by volatilization from the reaction mixture. Dry formaldehyde or a substance yielding formaldehyde, including polymeric formaldehydes, such as trioxane and particularly paraformaldehyde, is employed in the reaction mixture.

Besides sulfuric acid, other strong acids can be employed as catalysts in the process of the present invention, including strong mineral acids, e.g. hydrochloric and chlorosulfonic acids, and strong organic acids, e.g., trifluoroacetic acid and sulfonic acids such as benzenesulfonic acid, toluenesulfonic acid and methanesulfonic acid. A small amount of acid catalyst, e.g., 0.005–0.1 mol of acid per mol of the methylene-bis-acylamide, is usually sufficient in the present process. Excessively large amounts of such acid promote the production of products other than the desired tetrazocine compounds.

The liquid organic diluent employed should be inert to the reactants and is present in sufficient amount to provide a stirrable reaction mixture. Suitable liquids of this type include hydrocarbons and chlorinated hydrocarbons such as benzene, toluene, xylene, chlorobenzene, trichloroethane, and ethylene dichloride. When an organic liquid, such as benzene and toluene, is employed together with sulfuric acid or chlorosulfonic acid as the catalyst, it is possible that some sulfonation of such hydrocarbon may occur during the process. However, as noted previously, the resulting sulfonic acids are also effective acid catalysts for the present reaction.

The following example specifically illustrates an embodiment of the method for carrying out the process of the present invention.

EXAMPLE 130 grams (1 mol) of methylene-bis-acetamide m.p. 195—198°C., prepared as described in Synthesis 1,30 (1972), and 60 grams (2 mols) of paraformaldehyde were suspended in 10,000 ml of toluene. 1 gram (0.01 mol) of conc. sulfuric acid was added and the resulting mixture was heated rapidly to the boil and refluxed under ordinary pressure for 18 hours while removing water by azeotropic distillation by means of a Dean-Stark apparatus. The reaction mixture was then cooled to room temperature and a small amount of unreacted methylene-bis-acetamide was removed by filtration. The filtrate was concentrated under vacuum to a volume of 1500 ml at which point a white, crystalline precipitate was separated by filtration and dried (wt. 24 grams). This material was purified by recrystallization from a hexane-chloroform mixture to yield 23 grams of a white, crystalline solid, which was identified as pure TAT by comparison of its IR and NMR Spectra with those of an authentic sample.

The remaining solvent was removed from the filtrate leaving 124 grams of a syrup. NMR analysis of this syrup showed that it contained a trace of TAT, substantial amounts of TRAT together with a compound identified as N-hydromethylmethylene-bis-acetamide and smaller amounts of other NH- and OH- containing products. No attempt was made to separate any of these products.

While the present invention has been described in detail, it will be apparent to those skilled in the art that there are many variations possible without departing from the scope of this invention, which is limited only by the appended claims.

What is claimed is:

1. A process for preparing an octahydro-1,3,5,7-tetraalkanoyl-1,3,5,7-tetrazocine compound of the formula:

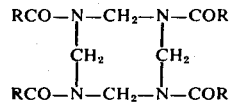

wherein R is an unsubstituted alkyl radical of 1 to 2 carbon atoms, which comprises the step of reacting a methylene-bis-alkanecarboxamide of the formula $CH_2(NHCOR)_2$ wherein R has the foregoing definition, with a polymeric formaldehyde of the group consisting of paraformaldehyde and trioxane, in an amount at least about one mol per mol of the methylene-bis-alkanecarboxamide in the presence of an acid catalyst of the group consisting of sulfuric acid, chlorosulfonic acid, hydrochloric acid, benzenesulfonic acid, toluenesulfonic acid, methanesulfonic acid and trifluoroacetic acid and an inert organic liquid diluent of the group consisting of benzene, toluene, xylene, chlorobenzene, trichloroethane and ethylene dichloride at a temperature within the range of 75°C. and 135°C., and removing the water as it is formed in the reaction by azeotropic distillation with the organic liquid.

2. The process of claim 1, wherein R is methyl.

3. The process of claim 2, wherein the polymeric formaldehyde is paraformaldehyde.

4. The process of claim 3, wherein the catalyst is sulfuric acid.

5. The process of claim 4, wherein the organic diluent is toluene.

* * * * *